(12) United States Patent
Cavezzan et al.

(10) Patent No.: US 10,421,905 B2
(45) Date of Patent: Sep. 24, 2019

(54) PROCESS FOR PREPARING A POLYMERIZATION INHIBITOR SOLUTION

(71) Applicant: RHODIA OPERATIONS, Paris (FR)

(72) Inventors: Jacques Cavezzan, Villeurbanne (FR); Sébastien Lomel, Saint Just Chaleyssin (FR); Christian Rouyer, Villefontaine (FR); Terry Chamberlain, Ternay (FR)

(73) Assignee: Rhodia Operations, Paris (FR)

( * ) Notice: Subject to any disclaimer, the term of this patent is extended or adjusted under 35 U.S.C. 154(b) by 23 days.

(21) Appl. No.: 15/550,478

(22) PCT Filed: Feb. 22, 2016

(86) PCT No.: PCT/EP2016/053627
§ 371 (c)(1),
(2) Date: Aug. 11, 2017

(87) PCT Pub. No.: WO2016/135076
PCT Pub. Date: Sep. 1, 2016

(65) Prior Publication Data
US 2018/0057740 A1 Mar. 1, 2018

(30) Foreign Application Priority Data
Feb. 23, 2015 (FR) .................................. 15 51504

(51) Int. Cl.
| | | |
|---|---|---|
| *C07C 7/20* | (2006.01) |
| *C09K 15/08* | (2006.01) |
| *C08F 2/42* | (2006.01) |
| *C08F 2/01* | (2006.01) |
| *C09K 15/26* | (2006.01) |

(52) U.S. Cl.
CPC ............... *C09K 15/08* (2013.01); *C07C 7/20* (2013.01); *C08F 2/01* (2013.01); *C08F 2/42* (2013.01); *C09K 15/26* (2013.01)

(58) Field of Classification Search
CPC ........................................................ C07C 7/20
See application file for complete search history.

(56) References Cited

U.S. PATENT DOCUMENTS 3,222,263 A 12/1965 Cambell
2013/0274519 A1* 10/2013 Mueller-Engel ....... B01D 3/225
562/600

FOREIGN PATENT DOCUMENTS

CN 102208564 A 10/2011

OTHER PUBLICATIONS

ChemSpider. "Mequinol." (Apr. 16, 2014). Accessed Sep. 3, 2018. Available from: < http://www.chemspider.com/Chemical-Structure.8665.html >. (Year: 2014).*
Chemical Book. "4-Methoxyphenol." (Sep 9, 2013). Accessed Sep. 3, 2018. Available from: < http://www.chemicalbook.com/ChemicalProductProperty_EN_CB7853133.htm >. (Year: 2013).*

* cited by examiner

Primary Examiner — Noble E Jarrell
Assistant Examiner — John S Kenyon

(57) ABSTRACT

The invention relates to a process for preparing concentrated solutions of polymerization inhibitor, that can be used for the production, purification and storage of monomer compositions. This process comprises a step in which at least one polymerization inhibitor in the molten state is mixed with a solvent.

16 Claims, 1 Drawing Sheet

PROCESS FOR PREPARING A POLYMERIZATION INHIBITOR SOLUTION

CROSS-REFERENCE TO RELATED APPLICATION

This application is a U.S. national stage entry under 35 U.S.C. § 371 of International Patent Application No. PCT/EP2016/053627, filed Feb. 22, 2016, which claims priority to French Patent Application No. 1551504, filed on Feb. 23, 2015, the whole content of each of these applications is hereby incorporated herein by reference for all purposes.

TECHNICAL FIELD OF THE INVENTION

The present invention relates to the field of polymerization inhibitors. More specifically, this invention relates to a process for preparing concentrated solutions of polymerization inhibitor, that can be used for the production, purification and storage of monomer compositions.

PRIOR ART

Polymerization inhibitors are chemical compounds capable of delaying or preventing polymerization reactions between monomers. They are therefore compounds which are widely used in industry and are added to monomers to facilitate and make safe the storage, transport or distillation thereof. Most polymerization inhibitors have melting points above ambient temperature and they are generally in solid form, for example in the form of powders, flakes, pellets, extruded materials, spheres, beads or chips, having variable shapes and sizes. When they are used, these polymerization inhibitors are typically dissolved in a solvent so as to form a concentrated solution of polymerization inhibitor. This concentrated solution, the concentration of which is fixed and known, is then added to containers of monomers or during the steps of preparing, transforming or purifying the monomers. The solvent used to dissolve the solid polymerization inhibitor may be the monomer itself, as described in patent application US 2007/0167650, or else another solvent, such as water or an organic solvent.

American U.S. Pat. No. 6,899,452 describes, for example, a device and a process for preparing a polymerization inhibitor solution. In order to avoid the problems associated with unloading and adjusting the concentration of the solution with a powdered polymerization inhibitor, this document provides specific means suitable for the unloading and dissolution of a solid polymerization inhibitor in a solvent. Despite this, it is noted that the prior art processes still pose problems in terms of safety and working conditions. The pulverulent polymerization inhibitor is generally unloaded by hand, and creates dust that is dangerous to the health of the operators and to the safety of the industrial site.

Besides, American U.S. Pat. No. 3,222,263 discloses a method for inhibiting the polymerization of vinyl aromatic hydrocarbon, typically styrene, during distillation. Said method consists in introducing a minor amount of molten sulphur into a distillation system for the purification of a vinyl aromatic hydrocarbon. The object of this method is to precisely control the added amount of sulphur into the distillation system so as to obtain an effective inhibition of the polymerization and to minimize the losses of styrene. Said document does not suggest the preparation of any concentrated polymerization inhibitor solution, which could be used at any steps of preparing, transforming, purifying, storing or transporting the monomers.

It is in this context that the inventors have sought a process which makes it possible to obtain a polymerization inhibitor solution that is easier to use, and to overcome one or more of the prior art drawbacks.

BRIEF DESCRIPTION OF THE INVENTION

A subject of the invention is a process for preparing a polymerization inhibitor solution, comprising a step in which at least one polymerization inhibitor in the molten state is mixed with a solvent. The polymerization inhibitor is selected from the group consisting of p-methoxyphenol, 4-tert-butylcatechol, pyrocatechol, hydroquinone, benzoquinone, 2,4-dimethyl-6-tert-butylphenol, phenothiazine, copper dibutyldithio-carbamate, and mixtures thereof.

In addition, a subject of the invention is also a process for preparing a polymerization inhibitor solution, comprising the steps in which a polymerization inhibitor is melted, and then at least said polymerization inhibitor in the molten state is mixed with a solvent.

DESCRIPTION OF THE INVENTION

Figure 1:
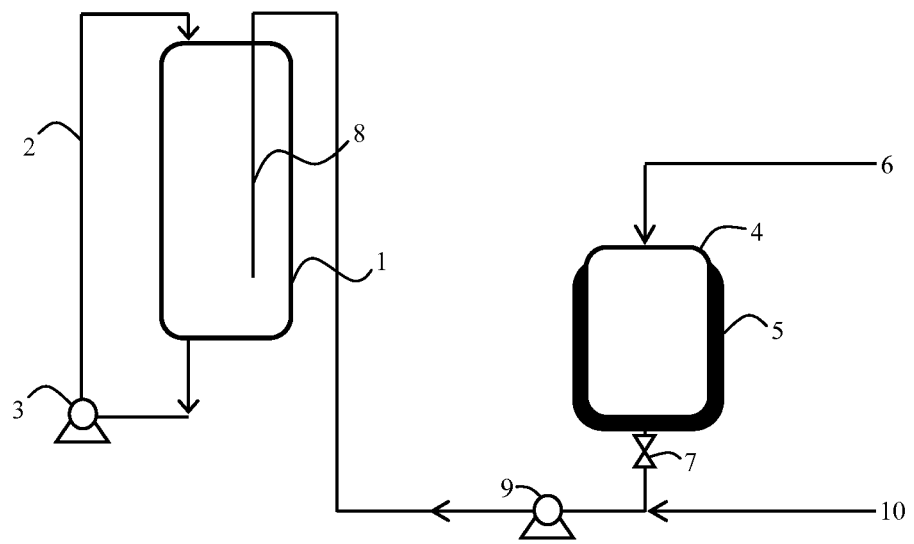
FIG. 1 represents a first embodiment of the process according to the invention, in which the polymerization inhibitor in the molten state is mixed with the solvent by means of a dip tube.

In the following description, the expression "between . . . and . . . " should be understood as including the mentioned limits.

In the present invention, a polymerization inhibitor is a compound intended to delay and/or prevent the polymerization of monomers, for example the radical polymerization of ethylenically unsaturated monomers.

At ambient temperature, said polymerization inhibitor according to the invention is in the solid state. According to the invention, ambient temperature is defined by a temperature range which generally ranges from 10° C. to 30° C., preferentially from 15° C. to 30° C. and more preferentially from 15° C. to 25° C. However, ambient temperatures that are more extreme are not excluded: the ambient temperature may, for example, reach −15° C. or −20° C. in some places in winter. Ambient temperature can in this case be defined by a temperature range which ranges from −20° C. to 10° C., preferentially from −15° C. to 0° C. The polymerization inhibitor according to the invention has a melting point (also called melting temperature, denoted $T_m$) above 15° C. $T_m$ is preferably above 25° C., more preferably above 35° C., and even more preferably above 50° C. Advantageously, $T_m$ may be below 200° C., more preferably below 150° C., and even more preferably below 130° C.

The polymerization inhibitor may be selected from the groups consisting of phenolic compounds, amines, nitro compounds, phosphorus- or sulfur-based compounds, hydroxylamines, compounds which have a nitroxyl radical, inorganic salts, and mixtures thereof. Among the polymerization inhibitor compounds of phenolic compound type, mention may be made of p-methoxyphenol, 4-tert-butylcatechol, pyrocatechol, hydroquinone, benzoquinone and 2,4-dimethyl-6-tert-butylphenol (also called Topanol A). Mention may also be made of phenothiazine and copper dibutyldithiocarbamate. The polymerization inhibitor used in the invention may be a pure compound, preferably selected from the group consisting of p-methoxyphenol, hydroquinone and 4-tert-butylcatechol. Quite particularly, it is p-methoxyphenol (denoted PMP). However, it is not out of the question for this polymerization inhibitor to be a mixture of several compounds which are themselves polymerization inhibitors, or else a compound essentially made up of one or more polymerization inhibitor compounds and additives, with the additives representing preferably less than 10% by weight, more preferably less than 5% by weight, and even more preferably less than 1% by weight of the total composition. It may for example be a eutectic compound, obtained from several compounds. According to the present invention, the polymerization inhibitor is selected from the group consisting of p-methoxyphenol, 4-tert-butylcatechol, pyrocatechol, hydroquinone, benzoquinone, 2,4-dimethyl-6-tert-butylphenol, phenothiazine, copper dibutyldithiocarbamate, and mixtures thereof.

Contrary to the prior art processes in which the polymerization inhibitor solution is prepared by dissolving at least one solid polymerization inhibitor in a solvent, the process according to the invention proposes preparing this mixture with a polymerization inhibitor in the molten state. The molten state denotes the state of a compound brought to a temperature above its melting point. A polymerization inhibitor in the molten state therefore differs, on the one hand, from a polymerization inhibitor in the solid state and, on the other hand, from a polymerization inhibitor in solution. In the present disclosure, a compound can be considered to be molten when its viscosity is advantageously less than or equal to 100 Pa·s, preferably 1 Pa·s, and more preferably 10 mPa·s, measured by means of a Rheomat 30 viscometer for shear rates of $100 \text{ s}^{-1}$ to $500 \text{ s}^{-1}$.

The temperature of the polymerization inhibitor in the molten state is preferably above $T_m$, more preferentially above or equal to $T_m+10°$ C., and even more preferentially above or equal to $T_m+20°$ C. Furthermore, this temperature is preferably at most $T_m+100°$ C., more preferably $T_m+65°$ C. For example, the temperature of the polymerization inhibitor in the molten state may be between 65° C. and 155° C., more preferably between 75° C. and 120° C.

According to one particular embodiment, the polymerization inhibitor is kept in the molten state under an inert atmosphere. In the following disclosure, the expression "inert atmosphere" or "inert gas" denotes in particular any gas with an oxygen content lower than that of air. The inert atmosphere consists of a gas which may be selected from the group consisting of nitrogen, carbon dioxide, argon, depleted air, and mixtures thereof. The expression "depleted air" denotes air containing less than 20% oxygen. Preferably, the polymerization inhibitor is kept in the molten state under nitrogen. Preferably, the inert atmosphere has a low moisture content, for example a moisture content below 1000 ppm of water. Preferably, it is industrial nitrogen. In order to keep the polymerization inhibitor in the molten state under an inert atmosphere, the inhibitor can be placed in an inerted container connected, via its vent, to an inert gas feed. This embodiment is particularly advantageous in cases where the polymerization inhibitor is oxidation-sensitive. Indeed, some polymerization inhibitors, such as PMP, if they are left in an oxidizing medium, for example in air, react and the by-products formed may be colored. As it happens, the coloring of the compound is a significant problem since it can also lead to the coloring of the polymer composition resulting from the polymerization of the monomer, which can be highly undesirable depending on the final applications for the polymer composition.

In the present disclosure, the term "container" includes drums, bottom-unloading containers, and mobile tanks with top or bottom unloading. This container may have any structure enabling it to carry out its function, and may be insulated or not. Preferably, the container according to the invention is a container of IBC (intermediate bulk container) type, as is well known in the technical field. Various types of containers are commercially available, for example from the manufacturers GLI, SCHAFER or UCON. The volume of the container according to the invention may be between 50 l and 10 000 l, more preferably between 500 l and 2500 l. According to one embodiment of the invention, the container is a small container, the volume of which is preferably between 500 l and 2000 l.

In order to obtain a polymerization inhibitor solution according to the invention, at least one polymerization inhibitor is mixed with a solvent. In the context of the present invention, the nature of the solvent is not limited. It is chosen from liquids capable of diluting the polymerization inhibitor, preferably rapidly. The solvent is preferably chosen according to the intended use of the polymerization inhibitor solution obtained. The solvent may be selected from the group consisting of water, organic solvents and mixtures thereof. Among the organic solvents, the solvent used is very preferably an ethylenically unsaturated monomer. Advantageously, when the polymerization inhibitor solution obtained is used to stabilize an ethylenically unsaturated monomer, the solvent is this same ethylenically unsaturated monomer.

In the context of the present invention, an ethylenically unsaturated monomer is a monomer comprising at least one ethylenic unsaturation. Ethylenically unsaturated monomers comprise, in particular, aromatic ethylenically unsaturated monomers, halogenated unsaturated monomers, acrylic monomers, unsaturated resins, unsaturated amides, unsaturated ethers, and vinylpyridines.

Aromatic ethylenically unsaturated monomers that may be mentioned include styrene, α-methylstyrene, divinylbenzene, vinyltoluene, vinylnaphthalene, styrenesulfonic acids, and mixtures thereof.

Halogenated unsaturated monomers that may be mentioned include vinyl chloride, chloroprene, vinylidene chloride, vinylidene fluoride, vinyl fluoride, and mixtures thereof.

Acrylic monomers that may be mentioned include unsaturated acids typified by acrylic acid (AA), methacrylic acid (MAA), crotonic acid, maleic acid, fumaric acid, and maleic anhydride; acrylates typified by methyl acrylate, ethyl acrylate, n-butyl acrylate, 2-ethylhexyl acrylate, hydroxyethyl acrylate, hydroxypropyl acrylate, dimethylaminomethyl acrylate, or any other acrylate derivative; methacrylates (MA) typified by methyl methacrylate, butyl methacrylate, lauryl methacrylate, dimethylaminoethyl methacrylate, and stearyl methacrylate; acrylonitrile (ACN), acrolein, and mixtures thereof.

Unsaturated resins that may be mentioned include acrylated epoxy resins and polyethylene glycol diacrylate.

Unsaturated amides that may be mentioned include acrylamides, N,N-dimethylacrylamide, methylenebisacrylamide, and N-vinylpyrrolidone.

Unsaturated ethers that may be mentioned include vinyl methyl ether.

Other ethylenically unsaturated monomers that may be mentioned also include vinyl acetate, diethyl vinylphosphonate, and sodium styrenesulfonate.

According to one particular embodiment, the solvent is an ethylenically unsaturated monomer, preferably an ethylenically unsaturated monomer selected from acrylic monomers and acrylamide, and even more preferably selected from the group consisting of acrylic acid (AA), methacrylic acid (MAA), methyl acrylate, ethyl acrylate, methyl methacrylate, acrylonitrile (ACN), acrolein, acrylamides, and mixtures thereof.

When the solvent is an ethylenically unsaturated monomer, the latter can be stabilized.

Before it is mixed with at least one polymerization inhibitor, the solvent can be placed in a tank. According to one preferred embodiment, the tank is stirred. It may be equipped with a stirring rotor, in particular a stirring rotor selected from the group consisting of radial rotors, axial rotors, combination rotors, twin-flow rotors, mechanical blending rotors, and rotors suitable for viscous media or for media containing solids. In addition or alternatively, the tank may be equipped with an external recirculation circuit provided with a pump. Under the action of this pump, part of the fluid contained in the tank is withdrawn, circulated through an external pipe and reinjected into the reactor. This movement ensures the mixing of this part of the fluid, and more generally of all the fluid contained in the tank. It is possible to provide a heat exchanger on the external recirculation pipe, so as to keep the fluid at a desired temperature.

The conditions under which the solvent is kept in the tank depend on the nature of said solvent. Preferably, the solvent is at ambient temperature. It can be kept under air or under controlled atmosphere. In particular, when the solvent is a stabilized ethylenically unsaturated monomer, the tank containing the solvent can be kept under an oxygen-containing atmosphere in order to avoid any risk of unwanted polymerization.

During the implementation of the process according to the invention, the polymerization inhibitor in the molten state can be unloaded from a container to a tank containing the solvent. The unloading of the polymerization inhibitor in the molten state may be total or partial.

The step consisting in mixing at least one polymerization inhibitor in the molten state with a solvent according to the invention can be carried out according to any method known to those skilled in the art.

According to a first embodiment, the mixing step comprises the introduction of the polymerization inhibitor in the molten state into the solvent by means of a dip tube. This dip tube may be provided with a diffuser at its end. Said dip tube can be placed in the tank containing the solvent.

According to another embodiment, the mixing step comprises the online introduction of the polymerization inhibitor in the molten state into a solvent circulation or feed circuit. This introduction can be carried out by suction or discharge by a pump. The mixing can be improved by using a static mixer. In the static mixer family, mention may for example be made of simple mixers, such as elbow mixers or T-mixers, tangential jet mixers, impact jet mixers, injectors, recirculation nozzles or turbulence promoters. Moreover, the mixing can be improved by using a mixer with repeating units, such as the static mixers (Sulzer SMX, Kenics, etc.), a bulk bed of beads or particles, metallic or ceramic foams, etc.

The injection of the polymerization inhibitor into the solvent can be carried out using one or more pumps and/or using a gas pressure, preferably an inert gas pressure. The use of a gas pressure may be preferred. However, the container containing the polymerization inhibitor in the molten state must be capable of withstanding the gas pressure. With an optimal configuration, the injection of the polymerization inhibitor into the solvent can also be carried out by gravity.

One of the technical difficulties to be solved during the mixing step is that of preventing blocking of the injection system. Indeed, in order to be in the molten state, the polymerization inhibitor is kept at a temperature above its melting point, which is itself above ambient temperature. As it happens, the solvent with which the polymerization inhibitor is mixed is generally at ambient temperature. If the polymerization inhibitor encounters a cold point before it is diluted in the solvent, it can solidify and be deposited in the device.

Devices such as pipes which allow the polymerization inhibitor in the molten state to be conveyed can advantageously be thermally insulated and/or heated to prevent the formation of heated plugs, for example using a jacket or electrical tracing. When the mixing is stopped, a step of rinsing these devices can be carried out, for example with a pressurized gas, preferably a pressurized inert gas, or with solvent.

According to one embodiment, during the mixing step, the container containing the polymerization inhibitor and the tank containing the solvent together constitute a closed system. This embodiment is advantageous when it is not desired for the polymerization inhibitor and/or the solvent to be brought into contact with an uncontrolled atmosphere.

According to one preferred embodiment, the process also comprises a preliminary step in which said polymerization inhibitor is melted. A subject of the invention is also a process for preparing a polymerization inhibitor solution, comprising the steps in which a polymerization inhibitor is melted, and then at least said polymerization inhibitor in the molten state is mixed with a solvent. Advantageously, the polymerization inhibitor is contained in a container and said container can be heated using a heating means until said polymerization inhibitor is molten.

This heating means may be chosen from all the devices known to those skilled in the art which enable the temperature within the container to be modified. Just one or several identical or different heating means may be used simultaneously or alternately. The one or several heating means may be devices which are built into the container and which cannot be removed therefrom, or else removable devices which are connected to the container, or else devices which are separate from the container. The container may be thermally insulated from the ambient environment by its own insulation, or by any device separate from the container and capable of carrying out this function. According to a first embodiment, the container is equipped with a wall and preferably a bottom which have a jacket, in which a heat-transfer fluid can flow. The heat-transfer fluid may in particular be liquid water or steam. According to another embodiment, the container is provided with heating resistors. According to yet another embodiment, the heating means consists of a heating blanket or a heating shell which may be placed around the container when the latter is not insulated. According to yet another embodiment, the container is provided with a heating pin or coil, in which a heat-transfer fluid can flow. According to yet another embodiment, the heating means consists of an oven or a hot chamber in which the container may be placed.

The heating of the container may be controlled heating so as to advantageously avoid any degradation of the polymerization inhibitor. To avoid local overheating, the heating step can be carried out in such a way that the temperature of the heating means remains permanently below or equal to a certain temperature. According to the present invention, during the heating step, the temperature of the heating means remains below or equal to $T_m+105°$ C., and preferably $T_m+70°$ C., $T_m$ being the melting temperature of the polymerization inhibitor. In this way, the temperature of the heated walls of the container in contact with the polymerization inhibitor remains below or equal to $T_m+105°$ C., preferably $T_m+70°$ C. The implementation of the heating step depends in particular on the heating means used and on the nature of the fluids or mixture of fluids involved. Controlling the temperature of the heating means may be carried out in a known way by those skilled in the art as a function of the type of heating means used. For example, when the heating means consists of a heat-transfer fluid flowing through a jacket or a coil, the temperature of the heating means can be controlled via the temperature of the heat-transfer fluid. When the heating means consists of an electrical device, the temperature of the heating means may be controlled via the electric power supply. When the heating means consists of an oven or a hot chamber, the temperature of the heating means may be controlled via a thermostat that sets the temperature of this oven or hot chamber. According to one embodiment, the container is provided with a jacket and the step of heating consists in causing water between approximately 75° C. and approximately 95° C. or expanded steam between approximately 100° C. and approximately 160° C. to flow in the jacket of the container for a duration determined as a function of the ambient temperature and of the state of solidification of the product in the container. According to one particularly advantageous embodiment, the heating step is carried out under an inert atmosphere.

The concentration of polymerization inhibitor in the solution obtained after mixing can be typically between 0.1% and 30% by weight, preferably between 1% and 30% by weight, more preferably between 2% and 15% by weight.

Before, after or simultaneously with the mixing of at least one polymerization inhibitor in the molten state with a solvent, it is possible to add other compounds, for example one or more other polymerization inhibitor compounds, optionally in the molten state, or other additives. One or more additives may be selected from dispersants, detergents, antioxidants, antifoams, rust inhibitors, anticorrosives and surfactants. The dispersants can be selected from sulfonates, such as styrene sulfonate or naphthalene sulfonate, for instance the dispersant SUPRAGIL® MNS/90, which is a polyalkyl naphthalene sulfonate sold by Solvay; esters, such as the methyl ester of salicylic acid, also called methyl salicylate; succinimides, such as polyisobutenyl succinimide; tristyrylphenols, such as ethoxylated TSP and tristyrylphenol ethoxylate phosphate ester; acrylates, such as ethyl methacrylate, ethoxy methacrylate and 2-ethylhexyl acrylate; amides, such as dimethylamides, acrylamides, for instance N-tert-butylacrylamide or N-(butoxymethyl)methacrylamide; amines, such as isopropylhydroxylamine, Mannich bases, para-phenylenediamine and ortho-phenylenediamine; imidazoline, such as 1-aminoethyl-2-($C_{17}$ alkylene)-2-imidazoline; phenates, such as sulfurized calcium alkyl phenate; phosphates, such as sodium polyphosphates, for instance tripolyphosphates, phosphate esters, ethoxylated phosphate esters; and mixtures thereof. The detergents can be selected from salicylates, phenates and sulfonates. The antioxidants can be selected from amines and derivatives of phenol. The antifoams can be selected from silicones and acrylates. The rust inhibitors can be selected from amines, esters, derivatives of phenol, and sulfonates. The anticorrosives can be selected from nitrogenous compounds such as triazoles and thiadiazoles. The choice of these ancillary additives, and the adjustment of their respective amounts, are part of the competence of those skilled in the art.

The process for preparing a solution containing at least one polymerization inhibitor according to the invention can be carried out continuously or batchwise. In a continuous operation, a continuous feed of solvent can be mixed with a continuous feed of polymerization inhibitor in the molten state, while an amount of the solution obtained is continuously removed. In a batchwise operation, batches of solution are prepared. The polymerization inhibitor solution obtained at the end of the process according to the invention can be used in a known manner by those skilled in the art in any step for producing, purifying, storing and/or using a monomer, preferably an ethylenically unsaturated monomer. According to one embodiment, the process according to the invention also comprises a step comprising the injection of said solution containing at least one polymerization inhibitor obtained into an ethylenically unsaturated monomer, for example in a distillation device or in a storage means.

Figure 2:
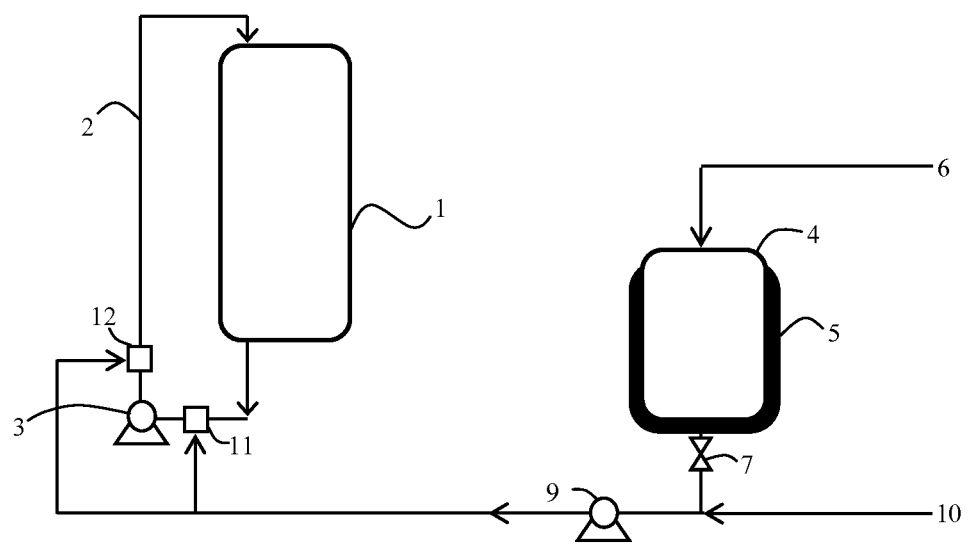
FIG. 2 represents a second embodiment of the process according to the invention, in which the polymerization inhibitor in the molten state is introduced into the solvent online, by means of a mixer.

The invention will be explained in greater detail by means of the two embodiments illustrated by FIGS. 1 and 2, given by way of nonlimiting illustration.

In FIG. 1, the tank 1 which contains a solvent suitable for diluting a polymerization inhibitor is provided with an external recirculation circuit 2. A pump 3 ensures the circulation and thus the mixing of the fluid contained in the tank 1. The container 4 which contains a polymerization inhibitor is equipped with a heating means 5 which may, for example, be an electrical device or a jacket in which a heat-transfer fluid circulates. By virtue of this heating means 5, the polymerization inhibitor is in the molten state in the container 4. The atmosphere inside the container 4 is kept inert through the injection of an inert gas 6. In order to perform the mixing according to the invention, the valve 7 is opened and the polymerization inhibitor is introduced into the tank 1 by means of a dip tube 8. The injection is carried out either by pressure of an inert gas 6, or by a pump 9, or by gravity if the container 4 is above the tank 1, or by a combination of these means. The unloading of the container 4 may be partial or total. When the mixing is finished, the valve 7 is closed and the device which has conveyed the polymerization inhibitor between the container 4 and the tank 1, quite particularly the dip tube 8, can be rinsed, for example by introducing a pressurized gas 10.

In another embodiment represented in FIG. 2, the mixing of the polymerization inhibitor in the molten state, contained in the container 4, in the solvent contained in the tank 1, is carried out online, by means of a mixer. The polymerization inhibitor is injected into the external recirculation circuit 2 of the tank 1. The injection can be carried out upstream and/or downstream of the pump 3. A dynamic or static mixer 11 or 12 located upstream or downstream of the pump makes it possible to ensure good mixing between the polymerization inhibitor and the solvent.

The invention claimed is:

1. A process for preparing a polymerization inhibitor solution, comprising mixing at least one polymerization inhibitor in the molten state with a solvent, wherein the at least one polymerization inhibitor is selected from the group consisting of p-methoxyphenol, 4-tert-butylcatechol, pyrocatechol, hydroquinone, benzoquinone, 2,4-dimethyl-6-tert-butylphenol, phenothiazine, copper dibutyldithiocarbamate, and mixtures thereof and wherein the at least one polymerization inhibitor is kept in the molten state under an inert atmosphere.

2. The process according to claim 1, wherein said at least one polymerization inhibitor consists of p-methoxyphenol.

3. The process according to claim 1, wherein said solvent comprises an ethylenically unsaturated monomer.

4. The process according to claim 3, wherein said solvent is selected from the group consisting of acrylic acid, methacrylic acid, methyl acrylate, ethyl acrylate, methyl methacrylate, acrylonitrile, acrolein, acrylamides, and mixtures thereof.

5. The process according to claim 1, wherein the temperature of the at least one polymerization inhibitor in the molten state is greater than or equal to $T_m+10°$ C. and less than or equal to $T_m+100°$ C., wherein $T_m$ represents the melting point of the at least one polymerization inhibitor.

6. A process for preparing a polymerization inhibitor solution, comprising mixing at least one polymerization inhibitor in the molten state with a solvent, wherein the at least one polymerization inhibitor is selected from the group consisting of p-methoxyphenol, 4-tert-butylcatechol, pyrocatechol, hydroquinone, benzoquinone, 2,4-dimethyl-6-tert-butylphenol, phenothiazine, copper dibutyldithiocarbamate, and mixtures thereof, and wherein the mixing step comprises the introduction of the at least one polymerization inhibitor in the molten state into the solvent by means of a dip tube.

7. A process for preparing a polymerization inhibitor solution, comprising mixing at least one polymerization inhibitor in the molten state with a solvent, wherein the at least one polymerization inhibitor is selected from the group consisting of p-methoxyphenol, 4-tert-butylcatechol, pyrocatechol, hydroquinone, benzoquinone, 2,4-dimethyl-6-tert-butylphenol, phenothiazine, copper dibutyldithiocarbamate, and mixtures thereof, and wherein the mixing step comprises the online introduction of the at least one polymerization inhibitor in the molten state into a solvent circulation or feed circuit.

8. The process of claim 1, further comprising, prior to mixing the at least one polymerization inhibitor in the molten state with a solvent, the step of melting the at least one polymerization inhibitor.

9. The process according to claim 8, wherein the at least one polymerization inhibitor is contained in a container and said container is heated using a heating means until the at least one polymerization inhibitor is molten.

10. The process according to claim 9, wherein the heating of the container is controlled heating.

11. The process according to claim 1, wherein the concentration of the at least one polymerization inhibitor in the solution obtained after mixing is between 0.1% and 30% by weight.

12. The process according to claim 11, wherein the concentration of the at least one polymerization inhibitor in the solution obtained after mixing is between 1% and 30% by weight.

13. The process according to claim 12, wherein the concentration of the at least one polymerization inhibitor in the solution obtained after mixing is between 2% and 15% by weight.

14. The process according to claim 1, further comprising: introducing the solution containing the at least one polymerization inhibitor obtained after mixing into an ethylenically unsaturated monomer.

15. The process according to claim 5, wherein the temperature of the at least one polymerization inhibitor in the molten state is greater than or equal to $T_m+20°$ C. and less than or equal to $T_m+65°$ C.

16. The process according to claim 14, wherein the solution containing the at least one polymerization inhibitor obtained is introduced into the ethylenically unsaturated monomer in a distillation device or in a storage means.

* * * * *